United States Patent [19]

Devine et al.

[11] 4,345,469
[45] Aug. 24, 1982

[54] AIR TUNNEL DEVICE FOR THERMOHYGROMETER

[75] Inventors: James A. Devine, Norton; José A. Miletti, Townsend, both of Mass.

[73] Assignee: The United States of America as represented by the Secretary of the Army, Washington, D.C.

[21] Appl. No.: 193,772

[22] Filed: Oct. 3, 1980

[51] Int. Cl.³ .......................................... G01N 25/62
[52] U.S. Cl. ....................................... 73/338.6; 73/77
[58] Field of Search ............. 73/336, 335, 338, 338.6, 73/338.3, 77

[56] References Cited

U.S. PATENT DOCUMENTS 1,636,350  7/1927  Armstrong .................. 73/338.6
2,915,898  12/1959  Van Luik, Jr. ................. 73/77 X

FOREIGN PATENT DOCUMENTS 2206856  6/1974  France ........................ 73/77

Primary Examiner—Stuart S. Levy
Assistant Examiner—Joseph W. Roskos
Attorney, Agent, or Firm—William G. Gapcynski; Werten F. W. Bellamy; John M. Petruncio

[57] ABSTRACT

An air tunnel device is provided for use in combination with a thermohygrometer of the type where the change of resistance of the probe in response to changes in the ambient atmosphere is used to measure the temperature and humidity of the atmosphere. The device includes a housing which defines an air passageway therethrough, a probe support for mounting the probe of the thermohygrometer so that the probe is exposed to the air passagement in the housing and a fan mounted in the housing below the probe support for drawing air into the air passageway and thus providing air flow at a constant velocity past the probe.

1 Claim, 2 Drawing Figures

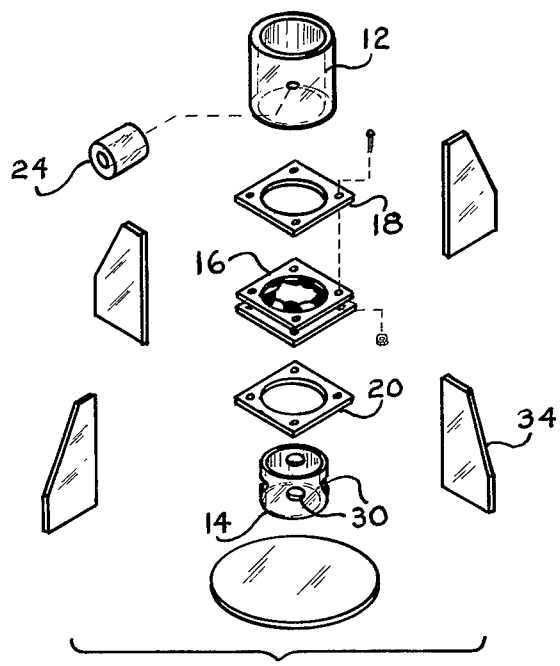
FIG. I
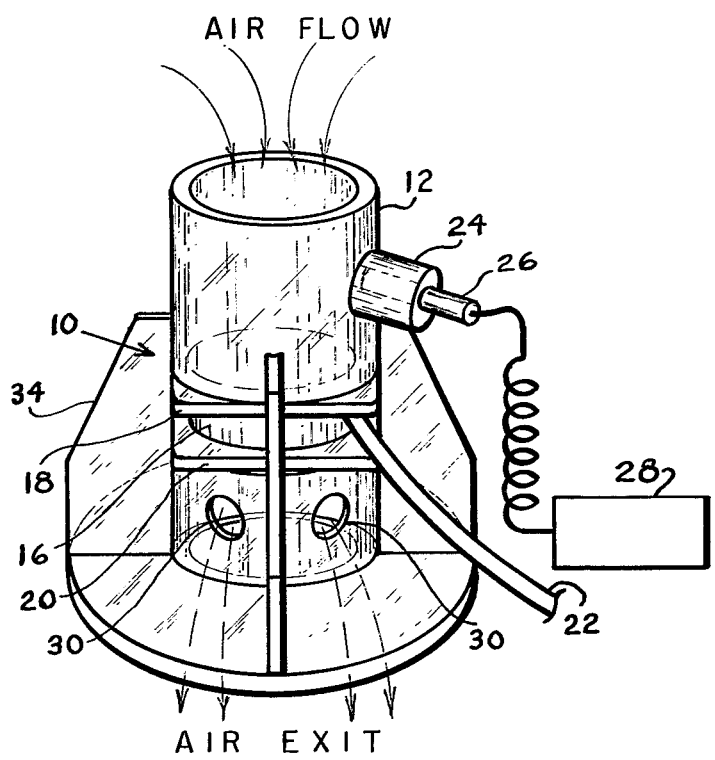
FIG. 2

AIR TUNNEL DEVICE FOR THERMOHYGROMETER

FIELD OF THE INVENTION

The present invention relates to thermohygrometer instruments which employ probes for measuring temperature and humidity and, more specifically, to an "air tunnel" device for use with such an instrument.

BACKGROUND OF THE INVENTION

Temperature/humidity measuring instruments such as the Wallac Thermohygrometer EP-400 Temperature/Humidity Instrument (LC-400/05 air probe) utilize the change in electrical resistance of an electrolytic film to measure humidity and rely on a sensing or measuring probe to detect this change. A problem with instruments of this type is that the current flow from the electrical measuring circuit through the probe sensor causes selfheating of the sensor which affects the reading (an increase in the reading of 1°-2° C. above ambient has been noted with the Wallac thermohygrometer). To combat this problem, it is suggested by the manufacturers of these instruments that the probe be swung back and forth evenly to create air flow (at least 0.5 meter/sec. in the Wallac thermohygrometer) so as to cancel the self-heating effect. However, tests have shown that this approach is less than satisfactory from a number of standpoints. Chief among these is the fact that swinging of the probes does not provide a steady constant air flow and thus does not produce reliable readings. Other problems which affect performance include the amount of time necessary to achieve stable readings, the lack of uniformity in swinging techniques and the difficulty in ascertaining when a final balance is reached.

SUMMARY OF THE INVENTION

In accordance with the invention, an "air tunnel" device is provided for use in combination with a thermohygrometer of the type discussed above. The air tunnel device provides a constant velocity flow of air past the sensing probe of the thermohygrometer and as a result provides stable, accurate measurements. The air tunnel of the invention overcomes problems associated with the use of a probe in still air (insufficient heat transfer results in either failure of the probe to achieve equilibrium with the ambient environment or, at best, to achieve equilibrium only after a protracted period) and with swinging of the probe as recommended by the manufacturer (measurement errors and lack of reproducibility of results) and provides significant improvement over the latter technique with respect to responsiveness, accuracy and reliability.

According to a preferred embodiment thereof, the air tunnel device of the invention comprises a housing including an air inlet and at least one air outlet therein and defining an air passageway between the inlet and outlet, a probe support member for supporting the probe of the thermohygrometer such that the probe is exposed to the air passageway in the housing, and a fan device, located in the housing and disposed below the probe support member, for drawing air through the air passageway in the housing at a uniform or constant rate. Positioning the fan below the probe eliminates problems with heating of the probe which would affect the measurement results. The housing advantageously comprises a pair of stacked cylinders with the fan being disposed between the upper and lower cylinders and the probe support member mounted on the upper cylinder. The air outlet is preferably provided by a plurality of openings in the lower cylinder. In this embodiment, the lower cylinder is mounted on a base and a plurality of circumferentially-spaced, upright support members are affixed to the base and to the cylinders.

Other features and advantages of the invention will be set forth in, or apparent from, the detailed description of the preferred embodiments which follows.

BRIEF DESCRIPTION OF THE DRAWINGS

FIG. 1 is an exploded perspective view of the air tunnel device of the invention; and FIG. 2 is a perspective showing of the air tunnel device as used in combination with a thermohygrometer, the latter being shown schematically.

DESCRIPTION OF THE PREFERRED EMBODIMENTS

Referring to FIGS. 1 and 2, exploded perspective and assembled perspective views of the air tunnel device of the invention are respectively shown in the two figures. The device includes a housing which is generally denoted 10 and includes an upper cylinder 12 and lower cylinder 14. A fan 16 is mounted between upper cylinder 12 and lower cylinder 14 by upper and lower mounting brackets or flanges 18 and 20. In an exemplary embodiment, fan 16 comprises a boxer fan (e.g., Pamotor Div., Model 4600 X, 115 VAC, Burdy Co. Burlingame, CA) and is mounted in an inverted orientation so as to direct the flow of air downwardly. The fan 16 is connected to a suitable motor (not shown) by a cord 22 (see FIG. 2). A variable autotransformer (not shown) is preferably used to control the speed of the fan 16 and thus control the air movement through the air tunnel.

Upper cylinder 12 includes a support collar or support 24 for the temperature/humidity air probe 26 of a thermohygrometer 28 shown schematically in FIG. 2, and probe support 24 is designed so as to permit full insertion of probe 26 into the air stream created by fan 16. The probe support collar 24 is located above fan 16 so as not to be subjected to temperature increases produced by fan operation.

Lower cylinder 14 includes a plurality of apertures 30 bored therein to permit exhausting of the air drawn in by fan 16. The lower cylinder is mounted on a base 32 and a plurality of circumferentially spaced upright supports 34 are affixed to the sides of the cylinders 12 and 14.

In operation, fan 16 pulls or draws air at a uniform rate through upper cylinder 12 past probe 26, the air exhausting out of openings 30 in lower cylinder 14. As stated above, a variable autotransformer (e.g., Staco, Inc. Model 2PF1210, 120 VAC, 12 amps., Dayton, OH) can be used to adjust the air velocity and an anemometer (e.g., Davis Instrument, Model MD-62-B-80, 120 VAC, Baltimore, Md.) can be used to measure air velocity and enable the air velocity to be adjusted to an optimum value.

The air tunnel of the present invention was tested in relation to the Wallac thermohygrometer EP-400 instrument referred to above. Comparisons were made (i) with the probe static (and no air tunnel), (ii) with swinging of the probe as provided for in the instruction manual for the thermohygrometer and (iii) using the air channel of the invention, under a number of different conditions. The results of tests show that the air tunnel provides substantially improved results particularly with respect to responsiveness, accuracy, reliability and reproducibility of results.

Although the invention has been described in relation to exemplary embodiments thereof, it will be understood by those skilled in the art that variations and modifications can be effected in these exemplary embodiments without departing from the scope and spirit of the invention.

I claim:

1. In combination with a thermohygrometer instrument for temperature and humidity measurement of the type which includes a temperature/humidity air probe for detecting the temperature and humidity of the ambient air through the change of electrical resistance of the probe, an air tunnel device comprising a housing defining a central air passageway therein, a probe support member for receiving the temperature/humidity air probe of the thermohygrometer instrument and for mounting said probe so the probe is exposed to the air in said air passageway, said housing comprises upper and lower cylinders, a base affixed to the lower cylinder and upright reinforcement members spaced circumferentially about the housing and secured to the base of the cylinders wherein an upper intake opening and at least one lower exhaust opening and having a fan device located therein and disposed in said air passageway below the probe support member for drawing air in through said upper opening so as to create uniform velocity air flow past said probe.

* * * * *